United States Patent [19]
Pittet et al.

[11] Patent Number: 4,600,576
[45] Date of Patent: * Jul. 15, 1986

[54] THIOGERANYL ESTERS AND ORGANOLEPTIC USES THEREOF

[75] Inventors: Alan O. Pittet, Atlantic Highlands; Ranya Muralidhara, Fair Haven; Manfred H. Vock, Locust; Kevin P. Miller, Middletown; Domenick Luccarelli, Jr., Neptune, all of N.J.

[73] Assignee: International Flavors & Fragrances Inc., New York, N.Y.

[*] Notice: The portion of the term of this patent subsequent to Aug. 23, 2000 has been disclaimed.

[21] Appl. No.: 747,425

[22] Filed: Jun. 21, 1985

[51] Int. Cl.$^4$ .................. C07C 153/023; A61K 7/16; A61K 31/265; A23L 2/26
[52] U.S. Cl. ........................... 424/49; 426/535; 426/3; 252/522 R; 514/513; 558/250
[58] Field of Search .............. 260/455 R; 426/535, 426/3; 252/522 R; 424/49; 514/513

[56] References Cited

U.S. PATENT DOCUMENTS 3,879,562 4/1975 Pittet et al. .............. 260/455 R
4,400,390 8/1983 Pittet et al. .............. 260/455 R Primary Examiner—Henry H. Jiles
Assistant Examiner—Robert C. Whittenbaugh
Attorney, Agent, or Firm—Arthur L. Liberman

[57] ABSTRACT

Described is the genus of thiogeranyl esters defined according to the structure:

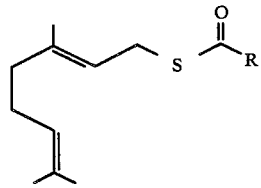

wherein R represents hydrogen, $C_1$–$C_5$ alkyl or $C_2$–$C_6$ alkenyl and uses thereof in augmenting or enhancing the aroma or taste of consumable materials including foodstuffs, chewing gums, toothpastes, medicinal products, perfume compositions, colognes and perfumed articles.

9 Claims, 11 Drawing Figures

NMR SPECTRUM FOR EXAMPLE I.

GLC PROFILE FOR EXAMPLE II.

FIG. 3 NMR SPECTRUM FOR EXAMPLE II.

GLC PROFILE FOR EXAMPLE III.
CRUDE

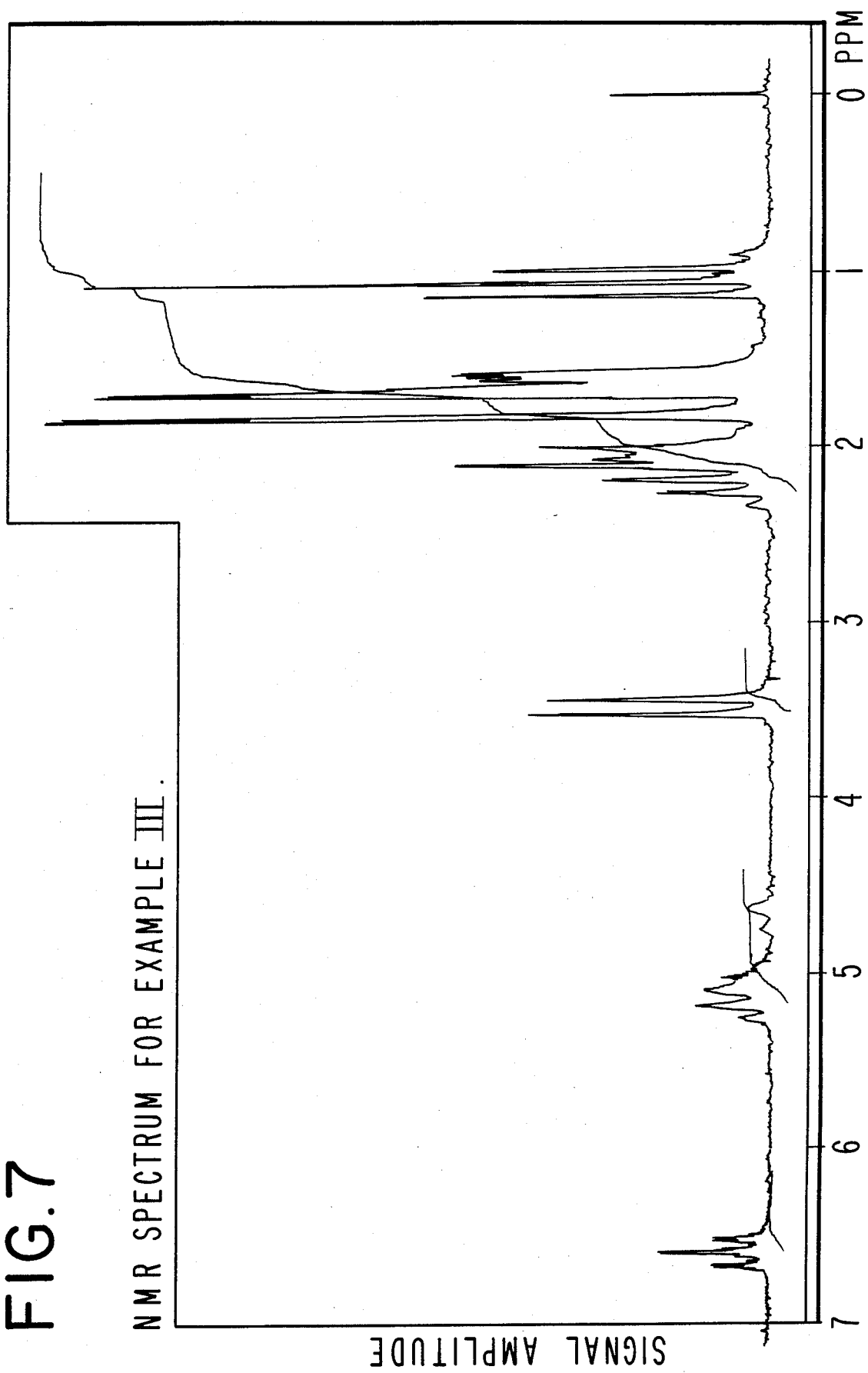
FIG. 7 NMR SPECTRUM FOR EXAMPLE III.

GLC PROFILE FOR EXAMPLE IV.
CRUDE

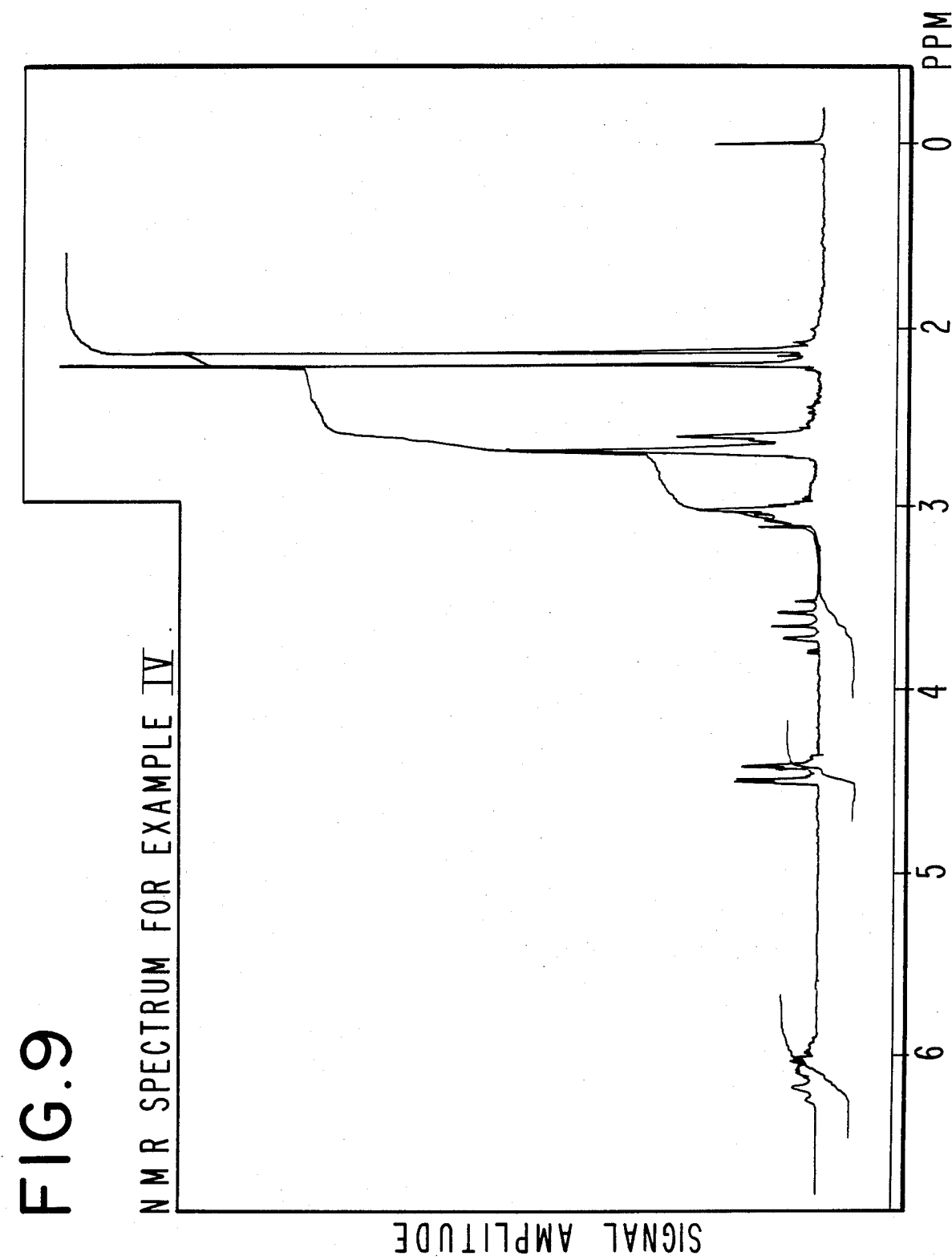
FIG. 9 NMR SPECTRUM FOR EXAMPLE IV

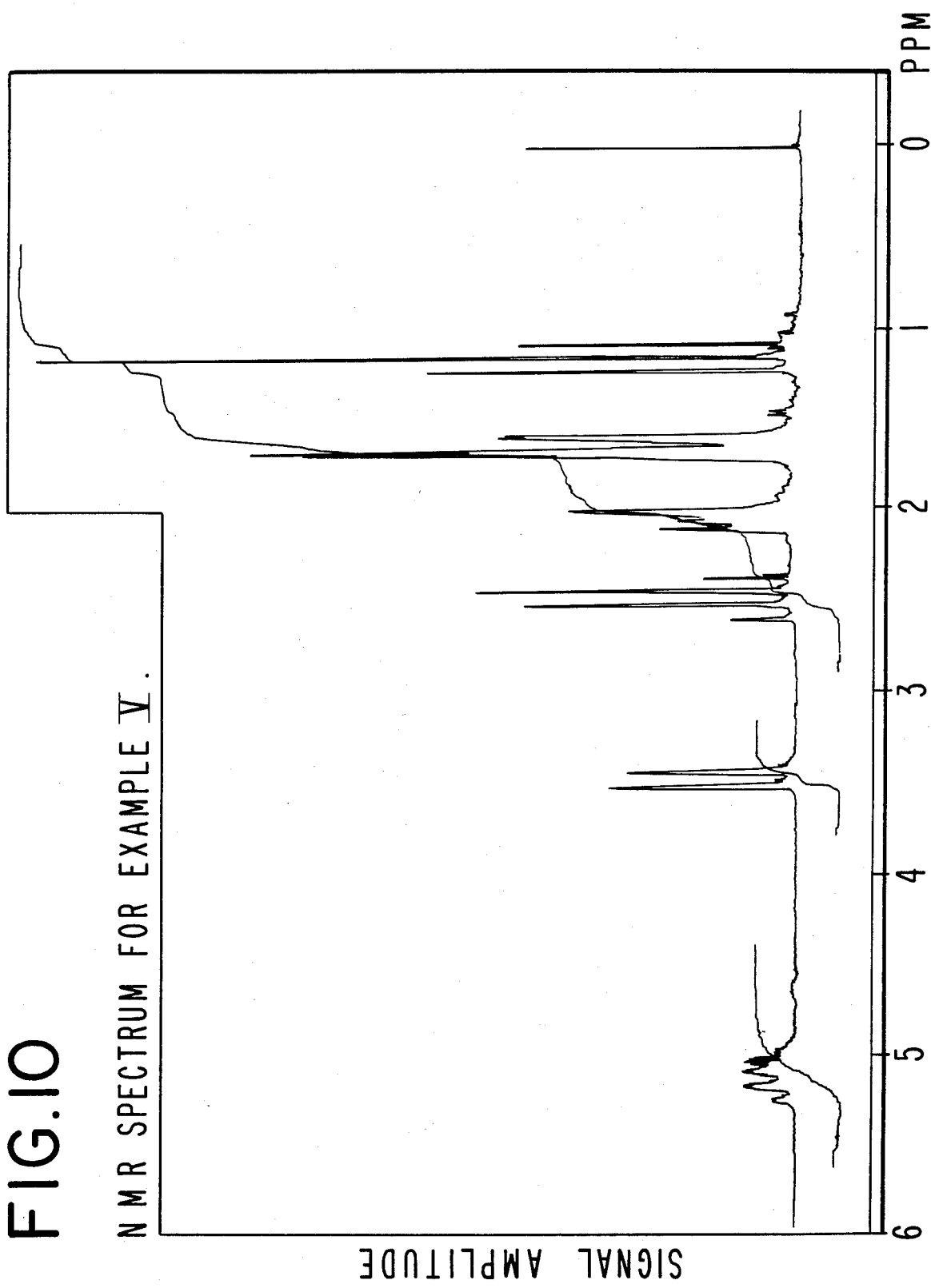

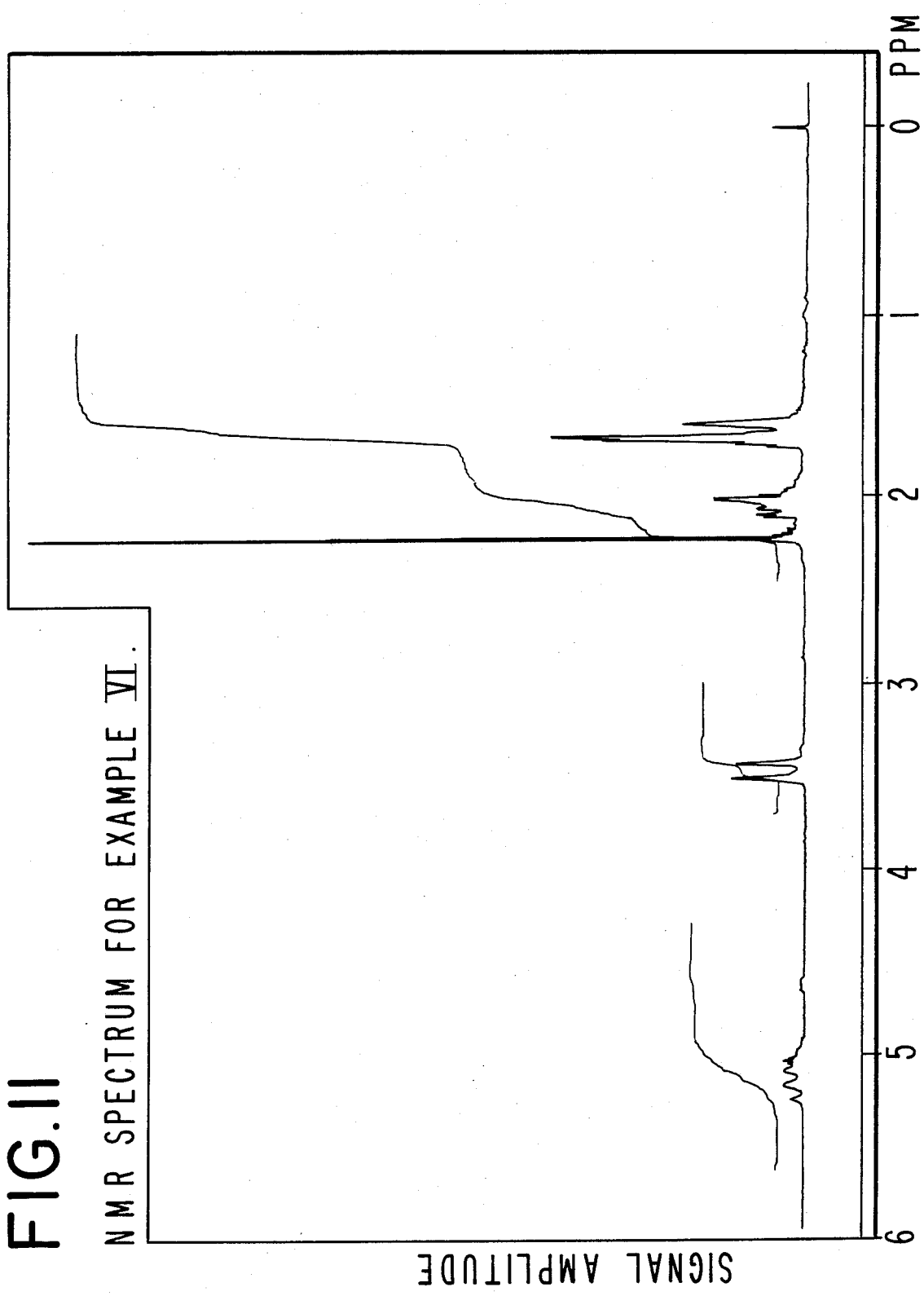

THIOGERANYL ESTERS AND ORGANOLEPTIC USES THEREOF

BACKGROUND OF THE INVENTION

This invention relates to thiogeranyl esters defined according to the generic structure:

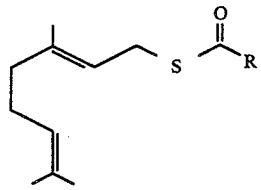

wherein R represents hydrogen, $C_1$–$C_5$ alkyl or $C_2$–$C_6$ alkenyl and uses thereof in augmenting or enhancing the aroma or taste of consumable materials including foodstuffs, chewing gums, toothpastes, medicinal products, perfume compositions, colognes and perfumed articles.

Artificial flavoring agents for foodstuffs have received increasing attention in recent years. In many areas, such food flavoring agents are preferred over natural flavoring agents at least in part, because of the uniform flavor that may be so obtained. For example, natural food flavoring agents such as extracts, essences, concentrates and the like are often subject to wide variations due to changes in quality and type and treatment of the raw materials. Such variations can be reflected in the end product and results in unreliable flavor characteristics and uncertainty as to consumer acceptance and cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is notable in products having floral, grapefruit, roasted, sulfuryl, fruity, oniony, carnation, guava, tomato and galbanum aroma and taste nuances.

Reproduction of floral, grapefruit, roasted, sulfury, fruity, oniony, carnation, guava, tomato and galbanum aroma and taste nuances has been the subject of long and continuous searches by those engaged in the production of foodstuffs. The severe shortage of food, especially protein foods, in many parts of the world has given rise to the need for utilizing non-meat sources of proteins and making such proteins as palatable as possible. Hence, materials which will closely simulate or exactly reproduce the flavor and aroma of gauva, tomato and grapefruit are required. Furthermore, meat flavors, vegetable flavors and fruit flavors have been enhanced previously by the use of such materials as monosodium glutamate. In many diets, sodium is not desired. Furthermore, in many diets, the use of glutamate ion or glutamic acid is highly undesirable. Therefore a need as arisen for a monosodium glutamate replacer and an alkali metal glutamate replacer which does not have any glutamate ion or any sodium ion present.

Food flavors in the thioalkanoic acid ester area are known in the prior art.

Thus, U.S. Pat. No. 4,426,403 discloses the genus of compounds defined according to the structure:

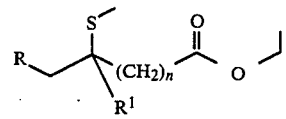

wherein R and R' represent hydrogen or $C_1$–$C_3$ alkyl as food flavorants, particularly in the fruity, vegetable or green pine needle aroma and taste area.

U.S. Pat. No. 3,870,800 relates to the processes for augmenting or enhancing the aroma or taste of foodstuffs using methylthio butanoic acid derivatives. U.S. Pat. No. 3,904,556, at Example XVII thereof states that ethyl-4-(methylthio)butyrate may be added to a cheese sauce to increase the notes usually present in the surface ripened cheese and to increase the cheese flavor intensity. In Example XX it is further stated that this compound, ethyl-4-(methylthio)butyrate is added to tobacco to enhance the pineapple character of a fruit flavor for tobacco.

U.S. Pat. Nos. 3,879,562 issued on Apr. 22, 1975 and the reissue patent thereof, RE 30,370 issued on Aug. 12, 1980 disclose the genus of compounds having the structure:

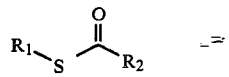

wherein $R_1$ represents alkyl, cycloalkyl, aryl, aralkyl, alkaryl, or alkenyl and $R_2$ represents alkyl, alkyl thioalkyl, aralkyl, alkaryl, or aryl in augmenting or enhancing the aroma or taste of various foodstuffs.

McFadden, et al, Analytical Chemistry 37,560, have suggested the presence of methyl thiohexanoate and thioheptanoate in oil derived from hops, and Buttery, et al, have reported similar work in J. Chromatography 18,399. Schultz, Day, and Libbey, "The Chemistry and Physiology of Flavors", Westport, Conn.:Avi. Publishing Company 1967, at page 412 disclose thioesters useful in flavoring.

In U.S. Letters Patent, Ser. No. 715,344 filed on Mar. 25, 1985 there is described in genus of mercapto-$C_2$–$C_3$ alkanoic acid esters of citronellol, geraniol and melanol defined according to the structure:

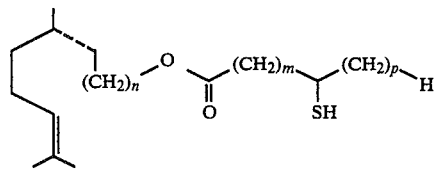

wherein N represents 0 or 1; M represents 0, 1 or 2; P represents 0 or 1; and the dashed line represents a carbon-carbon single bond or a carbon-carbon double bond with the proviso that when N is 0 then the dashed line represents a carbon-carbon single bond and uses thereof in augmenting or enhancing the aroma or taste of foodstuffs.

Furthermore, thiogeraniol (3,7-dimethyl-octa-2,6-dienyl mercaptan) having the structure:

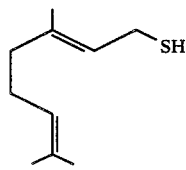

is disclosed as being useful in fragrances and flavors in U.S. Pat. Nos. 2,896,175 issued on July 22, 1975 and 3,996,387 issued on Dec. 7, 1976.

Nevertheless, nothing in the prior art discloses the thiogeranyl esters of our invention or their unexpected, unobvious and advantageous uses in augmenting or enhancing the aroma or taste of consumable materials, including foodstuffs, chewing gums, medicinal products, toothpastes, perfume compositions, perfumed articles or colognes.

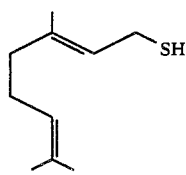

a precursor of the thiogeranyl esters of our invention (Conditions: Field strength: 100 MHz; Solvent: CFCl₃). The thiogeranyl having the structure:

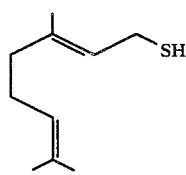

was produced according to Example I, infra.

Figure 2:
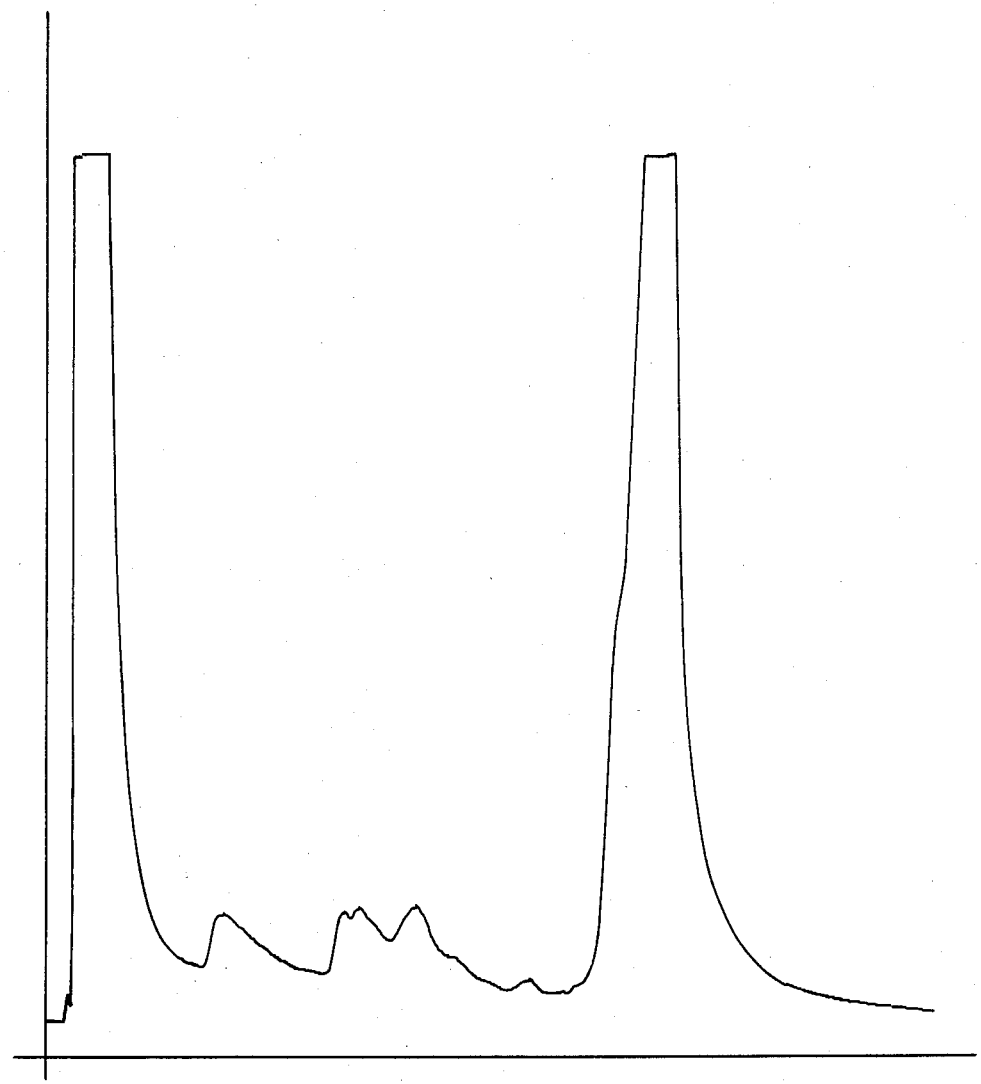

FIG. 2 is the GLC profile for the crude reaction product of Example II containing the compound having the structure:

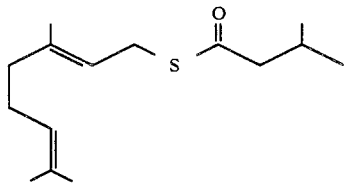

(Conditions: Carbowax column programmed at 120°–220° C. at 8° C. per minute).

Figure 3:
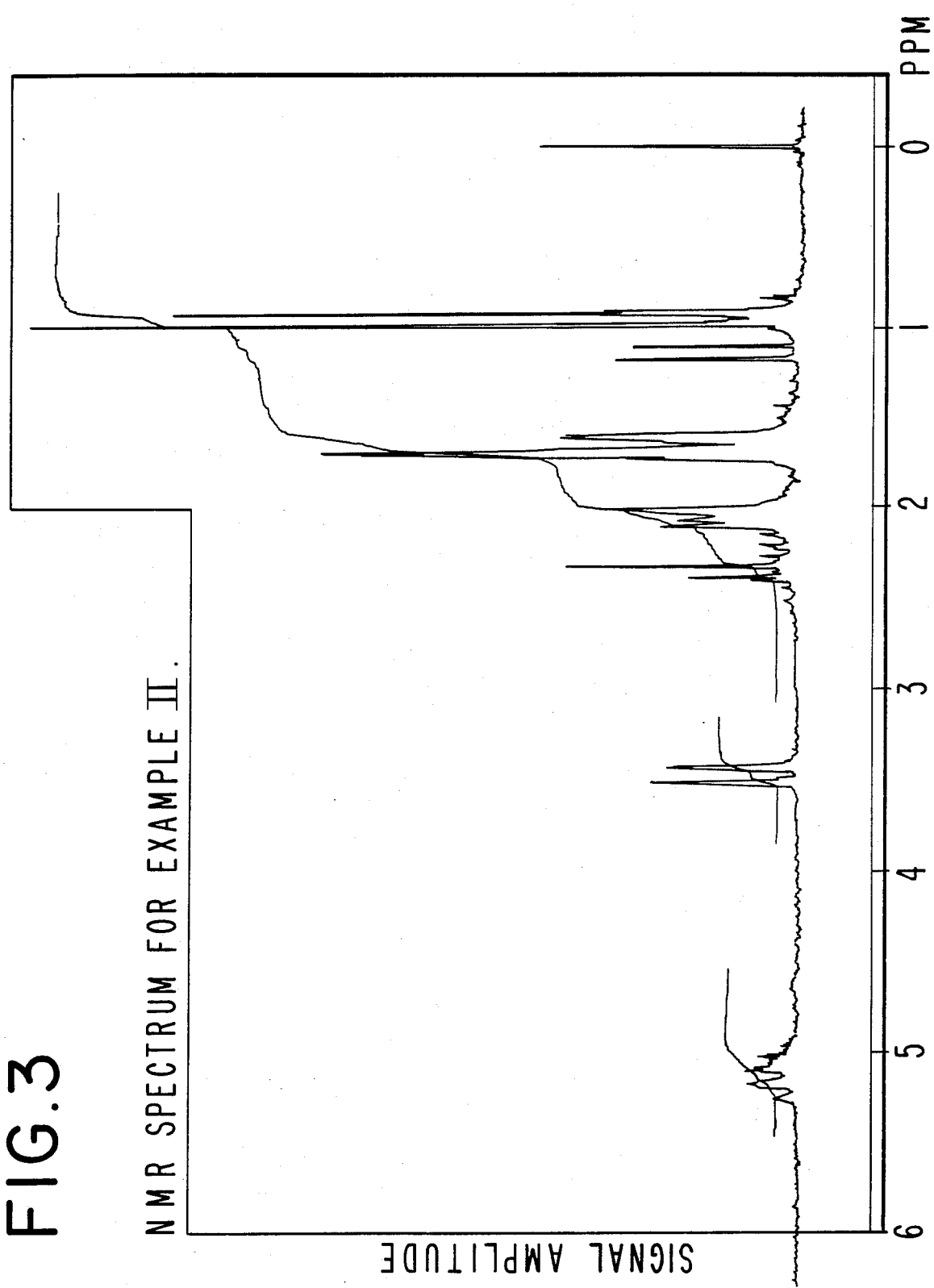

FIG. 3 is the NMR spectrum for the compound having the structure:

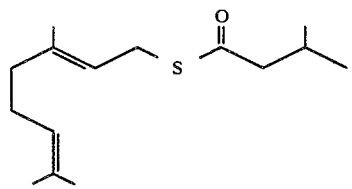

produced according to Example II (Conditions: Field strength: 100 MHz; Solvent: CFCl₃).

Figure 4:
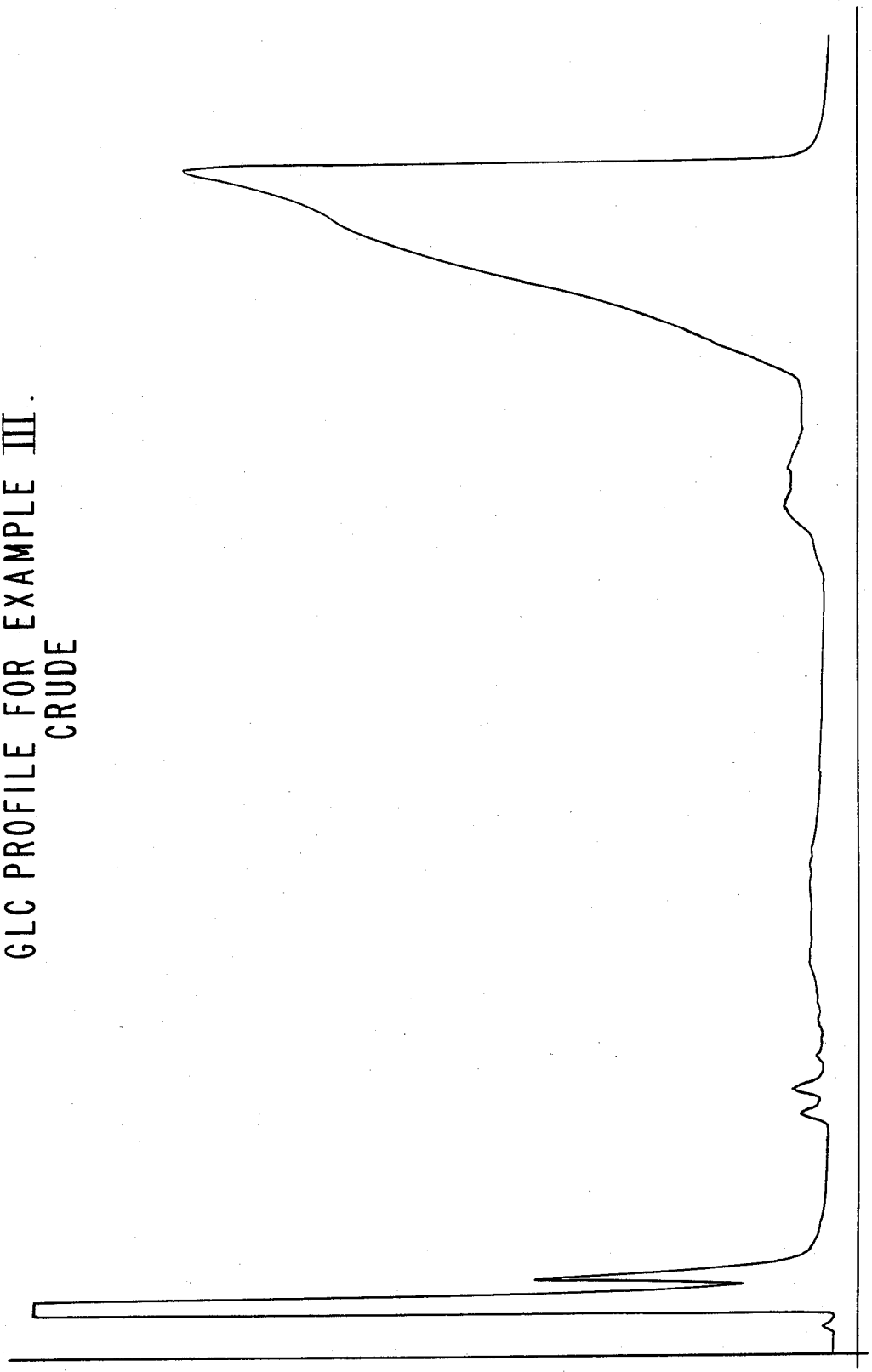

FIG. 4 is the GLC profile for the crude reaction product produced according to Example III containing the compound having the structure:

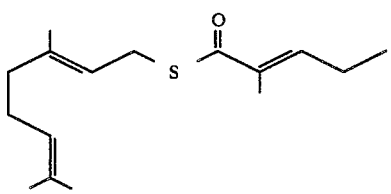

(Conditions: 8'×0.125" SE-30 column programmed at 100°–220° C. at 8° C. per minute).

Figure 5:
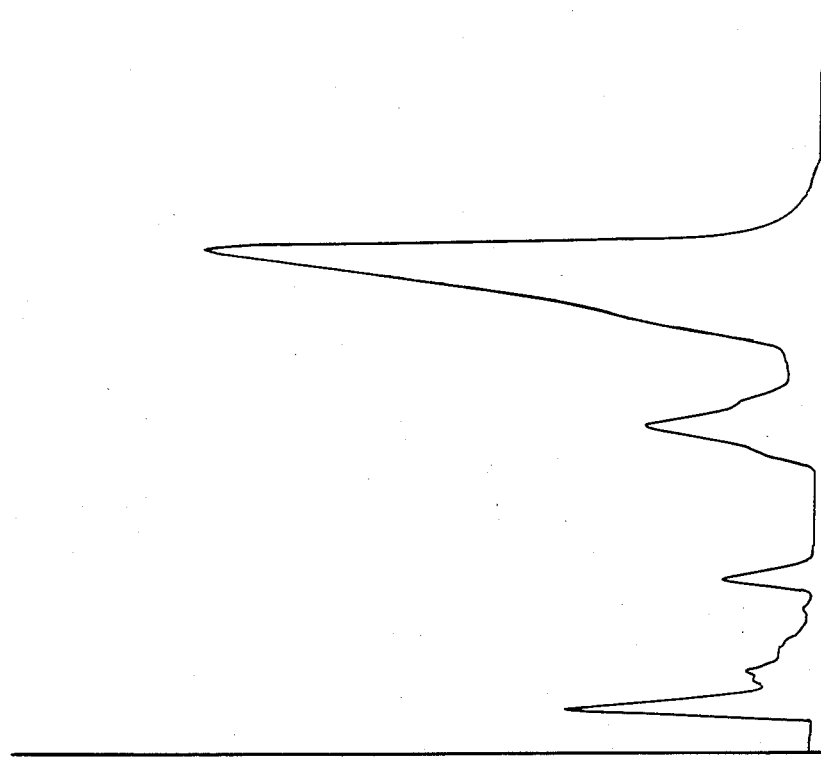

FIG. 5 is the GLC profile for Fraction 2 of the distillation of the reaction product of Example III containing the compound having the structure:

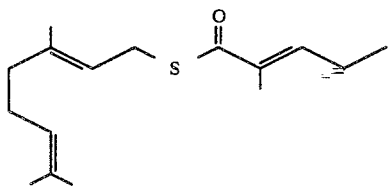

(Conditions: 8'×0.25" carbowax column programmed at 220° C. isothermal).

Figure 6:
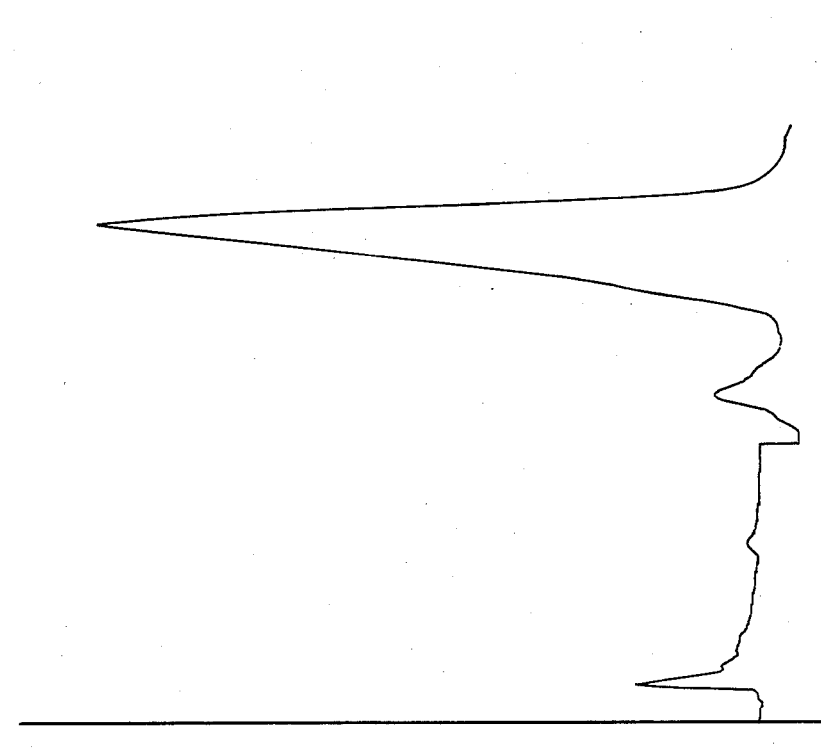

FIG. 6 is the GLC profile for Fraction 3 of the distillation of the reaction product of Example III containing the compound having the structure:

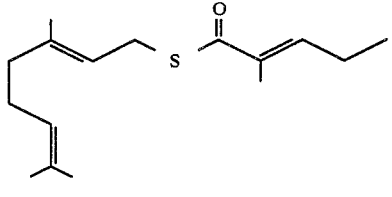

(Conditions: 8'×0.25" carbowax column programmed at 220° C. isothermal).

FIG. 7 is the NMR spectrum for the compound having the structure:

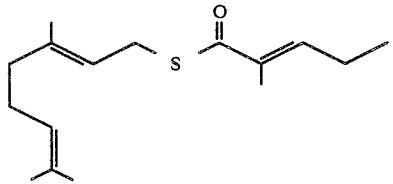

produced according to Example III (Conditions: Field strength: 100 MHz; Solvent: CFCl₃).

Figure 8:
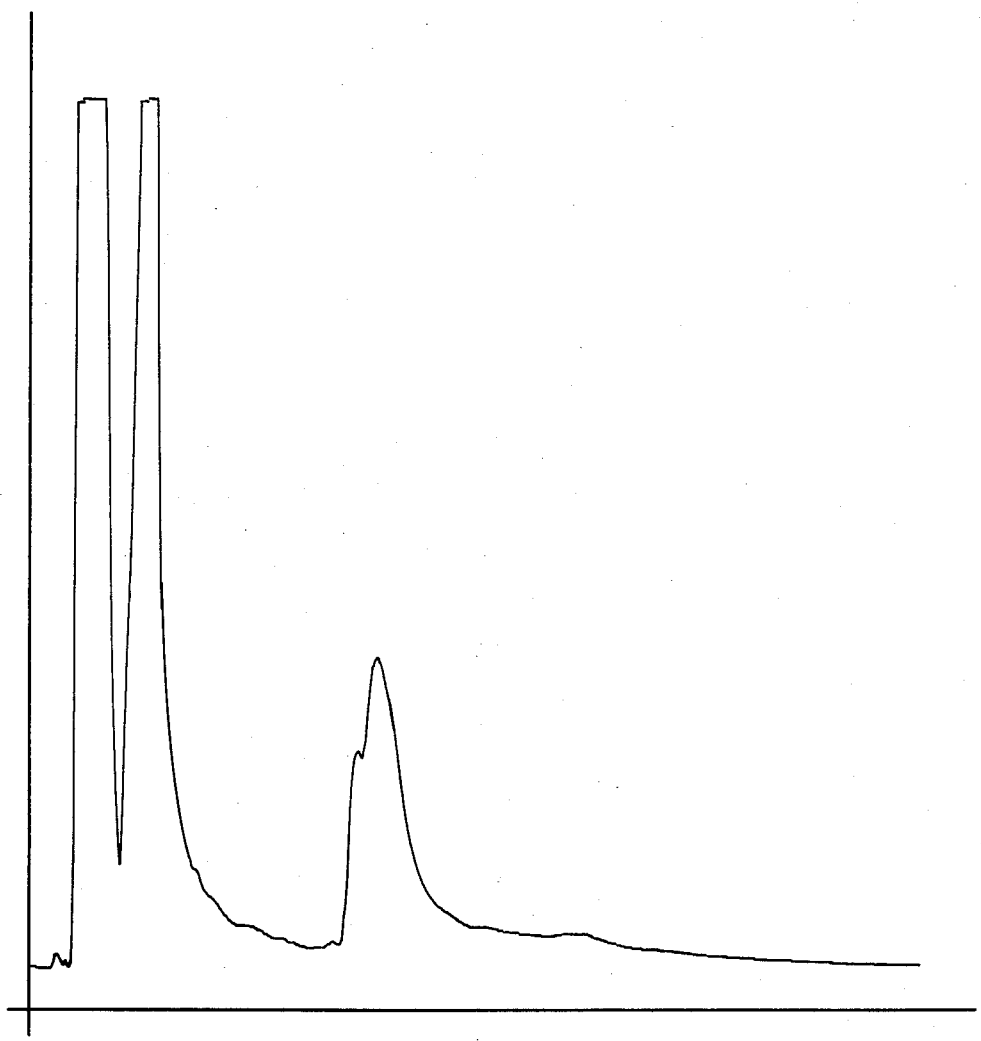

FIG. 8 is the GLC profile for the crude reaction product of Example IV containing the compound having the structure:

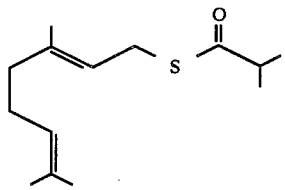

(Conditions: Carbowax column programmed at 100°–220° C. at 8° C. per minute).

FIG. 9 is the NMR spectrum for the compound having the structure:

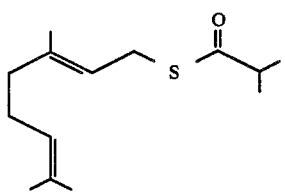

prepared according to Example IV (Conditions: Field strength: 100 MHz; Solvent: CFCl₃).

FIG. 10 is the NMR spectrum for the reaction product of Example V containing the compound having the structure:

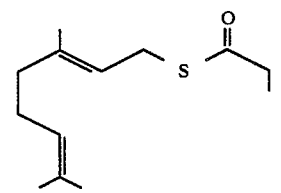

(Conditions: Field strength: 100 MHz; Solvent: CFCl₃).

FIG. 11 is the NMR spectrum for the compound having the structure:

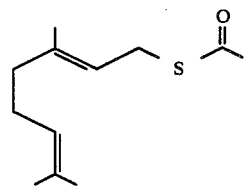

produced according to Example VI (Conditions: Field strength: 100 MHz; Solvent: CFCl₃).

THE INVENTION

The present invention provides thiogeranyl esters useful for augmenting or enhancing the aroma or taste of consumable materials including foodstuffs, chewing gums, medicinal products, toothpastes, perfume compositions, perfumed articles and colognes, said thiogeranyl esters being defined according to the structure:

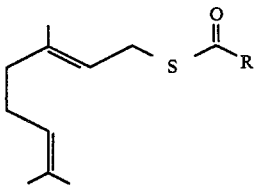

wherein R represents hydrogen, $C_1$–$C_5$ alkyl or $C_2$–$C_6$ alkenyl; as well as methods for augmenting, enhancing or modifying the organoleptic properties of such consumable materials, e.g., the taste and aroma of foodstuffs.

The thiogeranyl esters of our invention augment or enhance floral, grapefruit, roasted, sulfury, fruity, oniony, carnation, guava, tomato and galbanum aroma and taste nuances making them useful for augmenting or enhancing flavors for such foodstuffs as guava, tomato and grapefruit flavored foodstuffs.

The thiogeranyl esters of our invention may be prepared by reacting thiogeraniol having the structure:

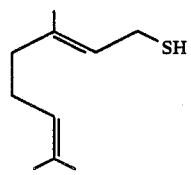

with an acyl halide according to the reaction:

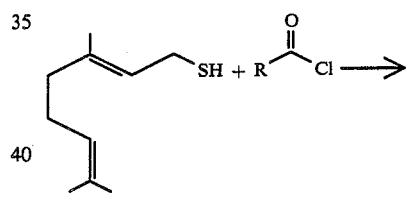

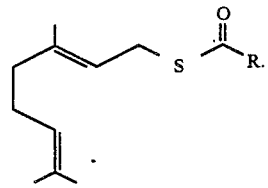

This reaction takes place in the presence of an alkyl amine catalyst, preferably triethylamine and in the presence of a solvent inert to both the reactants and the reaction products, for example, methylene dichloride. The reaction temperature is preferably at reflux conditions, e.g., at a temperature in the range of from about 50° C. up to about 100° C., depending upon the solvent used and the pressure over the reaction mass. The preferable pressure over the reaction mass is 1 atmosphere and the preferable solvent to be used is methylene dichloride. The range of concentration of the thiogeranyl in the solvent is between about 50 grams per liter up to about 100 grams per liter with a preferred thiogeraniol concentration of 75 grams per liter. The preferred concentration of catalyst, e.g., triethylamine in the solvent varies between 25 grams per liter and 100 grams per liter with a preferred catalyst concentration of about 50 grams per liter. The preferred concentration of acyl halide in the solvent may vary between about 20 grams per liter up to about 100 grams per liter. At the end of the reaction the reaction product is "worked-up" by means of water washing of the reaction product followed by fractional distillation. The distillation fractions recovered are those which are suitable for ingestion as food flavors or for use in placing on the skin, e.g., colognes. Accordingly, all traces of solvent and reactant must be completely removed.

The thiogeraniol may be prepared by any means well known to those having ordinary skill in the art, for example, those methods disclosed in U.S. Pat. Nos. 3,896,175 or 3,996,387, preferably by means of the reaction carried out in Example I, infra, which uses the following reactions:

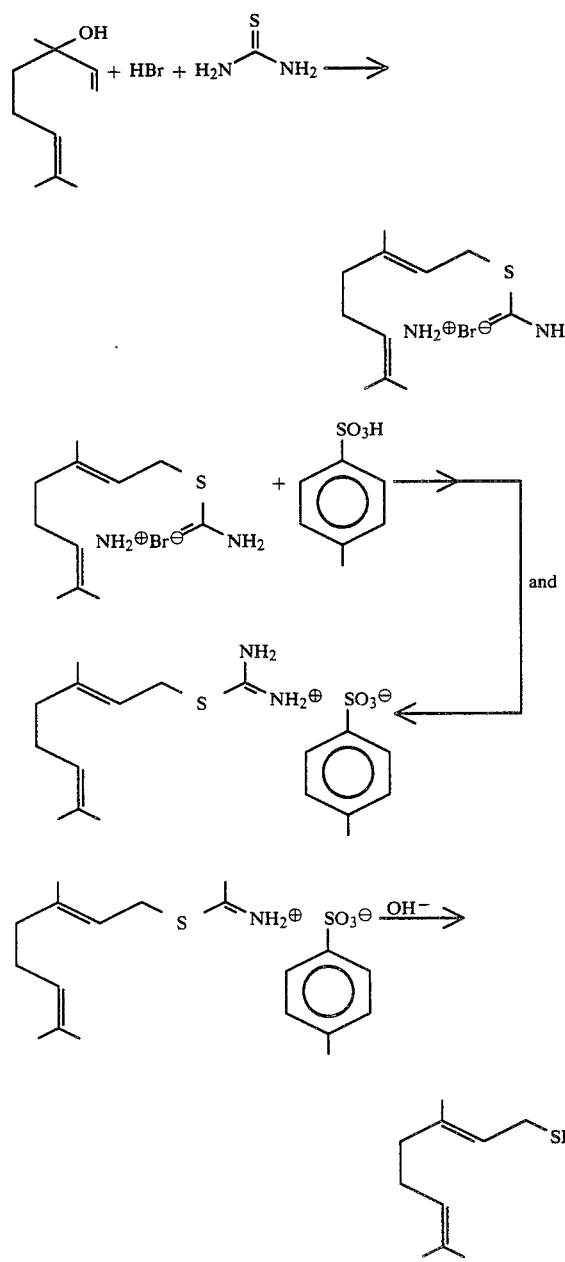

In the formula for the thiogeranyl esters of our invention, to wit:

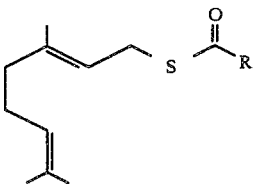

R may be exemplified, thusly:
Hydrogen;
Methyl;
Ethyl;
n-Propyl;
Isopropyl;
1-Butyl;
2-Butyl;
2-Methyl-propyl;
2-Methyl-butyl;
3-Methyl-butyl;
Vinyl;
Vinylmethyl;
Methylvinyl;
Ethylvinyl;
1-Methylbutenyl;
2-Methylbutenyl;
3-Methylbutenyl;
2-Butenyl;
3-Butenyl;
1-Pentenyl;
2-Pentenyl;
3-Pentenyl;
4-Pentenyl;
1-Methyl-1-pentenyl;
1-Methyl-2-pentenyl;
1-Methyl-3-pentenyl;
1-Methyl-4-pentenyl;
2-Methyl-1-pentenyl;
2-Methyl-2-pentenyl;
2-Methyl-3-pentenyl;
2-Methyl-4-pentenyl;
3-Methyl-1-pentenyl;
3-Methyl-2-pentenyl;
3-Methyl-3-pentenyl;
3-Methyl-4-pentenyl;
4-Methyl-1-pentenyl;
4-Methyl-2-pentenyl;
4-Methyl-3-pentenyl;
4-Methyl-4-pentenyl;
1-Ethyl-1-butenyl;
1-Ethyl-2-butenyl;
1-Ethyl-3-butenyl;
2-Ethyl-1-butenyl;
2-Ethyl-2butenyl;
2-Ethyl-3-butenyl;
1-Propyl-1-propenyl;
1-Propyl-2-propenyl;
2-Propyl-1-propenyl; and
2-Propyl-2-propenyl Examples of the products of our invention and their organoleptic properties are as follows:

| Structure of Compound | Organoleptic Properties |
| --- | --- |
| Compound having the structure: | A floral, grapefruit and roasted aroma |

| Structure of Compound | Organoleptic Properties |
|---|---|
| produced according to Example II. | and taste profile at 0.5 ppm. |
| Compound having the structure: [structure] produced according to Example III. | A sulfury, fruity, oniony and floral aroma and taste profile at 1 ppm. |
| Compound having the structure: [structure] produced according to Example IV. | A floral, carnation, guava and grapefruit aroma and taste profile at 1.0 ppm causing it to be useful in pineapple, grapefruit or guava flavored foodstuffs. |
| Compound having the structure: [structure] produced according to Example V. | A grapefruit and tomato aroma and taste profile at 0.5 ppm causing it to be useful in grapefruit, tomato and guava flavored foodstuffs. |
| Compound having the structure: [structure] produced according to Example VI. | A floral, sulfury, galbanum, fruity and grapefruit aroma and taste profile at 0.1 ppm causing it to be useful in mint and grapefruit-flavored foodstuffs. |

Thus, the thiogeranyl esters of our invention can be used to alter, vary, fortify, modify, enhance or otherwise improve the organoleptic properties including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such thiogeranyl esters of our invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the thiogeranyl esters of our invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-β-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl Acetate;
Maltol;
Ethyl butyrate;
Levulinic acid;
Piperonal;
Ethyl acetate;
n-Octanal;

n-Pentanal;
Hexanal;
Diacetyl;
Monosodium gluatmate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-dimethylfuran-3-thiol;
Hydrolyzed fish protein;
Tetramethyl pyrazine;
2-Sec butyl thiazole; and
Menthol.

The thiogeranyl esters or the compositions incorporating them, as mentioned above, can be combined with one or more vehicles or carriers for adding them to the particular product to be flavored. Vehicles can be edible or otherwise suitable materials such as ethyl alcohol, propylene glycol, water and the like. Carriers include materials such as gum arabic, carrageenan, guar gum, xanthan gum and the like. The thiogeranyl esters of our invention can be incorporated with the carriers by conventional means such as spray-drying, drum-drying, and the like. Such carriers can also include materials for coacervating the thiogeranyl esters of our invention (and other flavoring ingredients, as present) to provide encapsulated products. When the carrier is an emulsion, the flavoring composition can also contain emulsifiers such as mono- and diglycerides or fatty acids an the like. With these carriers or vehicles, the desired physical form of the composition can be prepared.

The thiogeranyl esters utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subject; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of thiogeranyl esters or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The amount of thiogeranyl esters of our invention to be utilized in flavoring compositions can be varied over a wide range depending upon the particular quality to be added to the foodstuff. Thus, amounts of one or more derivatives according to the present invention of from about 0.04 ppm up to 80 or 90 percent of the total flavoring composition can be incorporated in such compositions. It is generally found to be desirable to include from about 0.05 ppm up to about 0.1 percent of the thiogeranyl esters in such compositions.

One or more thiogeranyl esters prepared in accordance with the process of our invention and one or more auxiliary perfume ingredients including, for example, alcohols, aldehydes, ketones, terpenic hydrocarbons, nitriles, esters other than the thiogeranyl esters of our invention, lactones, natural essential oils and synthetic essential oils may be admixed so that the combined odors of the individual components produce a pleasant and desired fragrance, particularly, and preferably, in galbanum and other floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top-notes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, one or more thiogeranyl esters prepared in accordance with the process of our invention, can be used to alter, modify or enhance the aroma characteristics of a perfume composition, for example, by utilizing or moderating the olfactory reaction contributed by another ingredient in the composition.

The amount of one or more thiogeranyl ester prepared in accordance with the process of our invention which will be effective in perfume compositions as well as in perfumed articles (e.g., anionic, nonionic, cationic and zwitterionic solid or liquid detergents, soaps, fabric softener compositions, dryer-added fabric softener articles, optical brightener compositions and textile sizing agents) and colognes depends on many factors, including the other ingredients, their amounts and the effects which are desired. It has been found that perfume compositions containing as little as 0.01% of one or more thiogeranyl esters prepared in accordance with the process of our invention and less than 50% of one or more thiogeranyl esters prepared in accordance with the process of our invention or even less (e.g., 0.005%) can be used to impart a floral, citrus, minty and galbanum-like nuances to soaps, cosmetics, solid or liquid, anionic, cationic, nonionic or zwitterionic detergents, fabric softener compositions, fabric softener articles, optical brightener compositions, textile sizing compositions or other products. The amount employed can range up to 70% of the fragrance components and will depend on considerations of cost, nature of the end product, the effect desired on the finished product and the particular fragrance sought.

One or more thiogeranyl esters prepared in accordance with the process of our invention is useful (taken alone or together with other ingredients in perfume compositions) as (an) olfactory composition(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 0.2% of one or more thiogeranyl esters prepared in accordance with the process of our invention will suffice to impart a floral, minty, citrusy and galbanum aroma to galbanum and lavender formulations. Generally, no more than 6% of one or more of the thiogeranyl esters of our composition based on the ultimate end product is required in the perfumed article composition.

In addition, the perfume composition or fragrance composition of our invention can contain a vehicle or carrier for one or more thiogeranyl esters prepared in accordance with the process of our invention. The vehicle can be a liquid, such as a non-toxic alcohol, a non-toxic glycol, or the like. The carrier can also be an absorbent solid, such as a gum (e.g., gum arabic) or components for encapsulating the composition (such as gelatin) as by coacervation.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I

PREPARATION OF THIOGERANIOL

Reactions

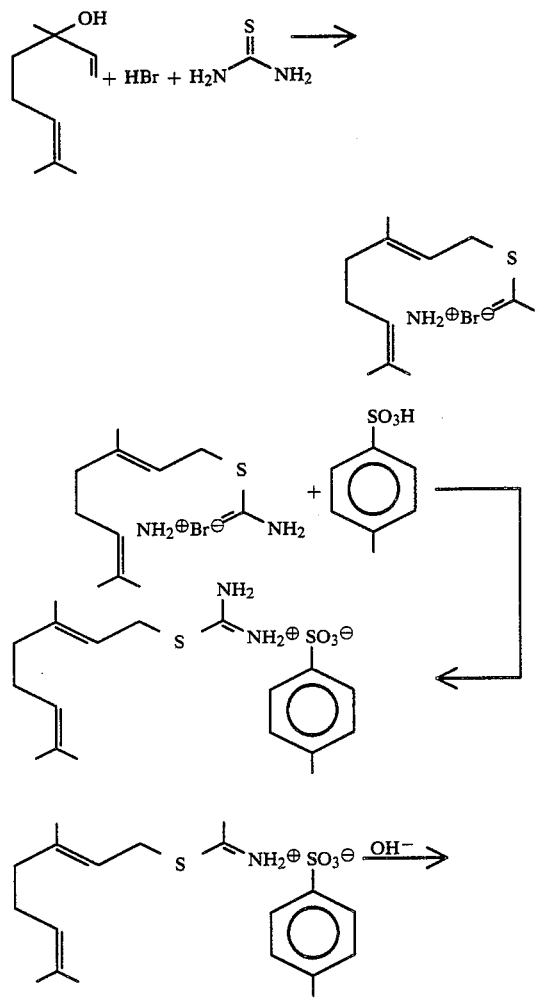

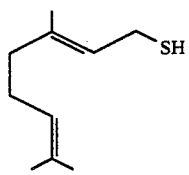

Into a 500 cc flask equipped with stirrer, thermometer, reflux condenser and addition funnel are placed 154 grams of linalool and 84 grams of thiourea. The resulting mixture is heated to 50° and over a two hour period through the addition funnel 124.5 ml of hydrobromic acid is added. The temperature of the reaction mass is maintained at 50° C. using heating. The reaction mass then exotherms to 65° C. At the end of the addition, the reaction mass is cooled to 15° C. and the reaction mass is split in half. The first half is combined with 200 ml 10% sodium hydroxide and the second half is combined with 96 grams of paratoluene sulfonic acid in 100 ml water with stirring. The first half is extracted with two 300 ml portions of methylene dichloride. The second half is filtered through a Buchner funnel and added to a beaker containing 200 ml sodium hydroxide solution (10%), stirred for 15 minutes and then extracted with three 250 ml portions of methylene dichloride. The resulting reaction mass is dried over anhydrous sodium sulfate and then distilled on a 1″ splash column at a vapour temperature of 140° C. and vacuum of 20 mm/Hg. pressure. The distillation product is then redistilled at a vapor temperature of 128°–130° C. at 5 mm/Hg. pressure on the 1″ splash column.

The resulting product is then redistilled on a Vigreux column yielding the following fractions:

| Fraction No. | Vapor Temp. (°C.) | Liquid Temp. (°C.) | Vacuum mm/Hg. Pressure |
|---|---|---|---|
| 1 | 130 | 166 | 6 |
| 2 | 137 | 174 | 7 |
| 3 | 122 | 174 | 8 |
| 4 | 127 | 181 | 7 |
| 5 | 108 | 184 | 8 |
| 6 | 128 | 204 | 7 |
| 7 | 118 | 234 | 8 |
| 8 | 75 | 228 | 7 |

Fractions 2–8 are bulked for subsequent reaction. The resulting product has the structure:

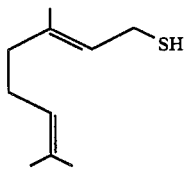

as confirmed by NMR, IR and mass spectral analyses.

Figure 1:
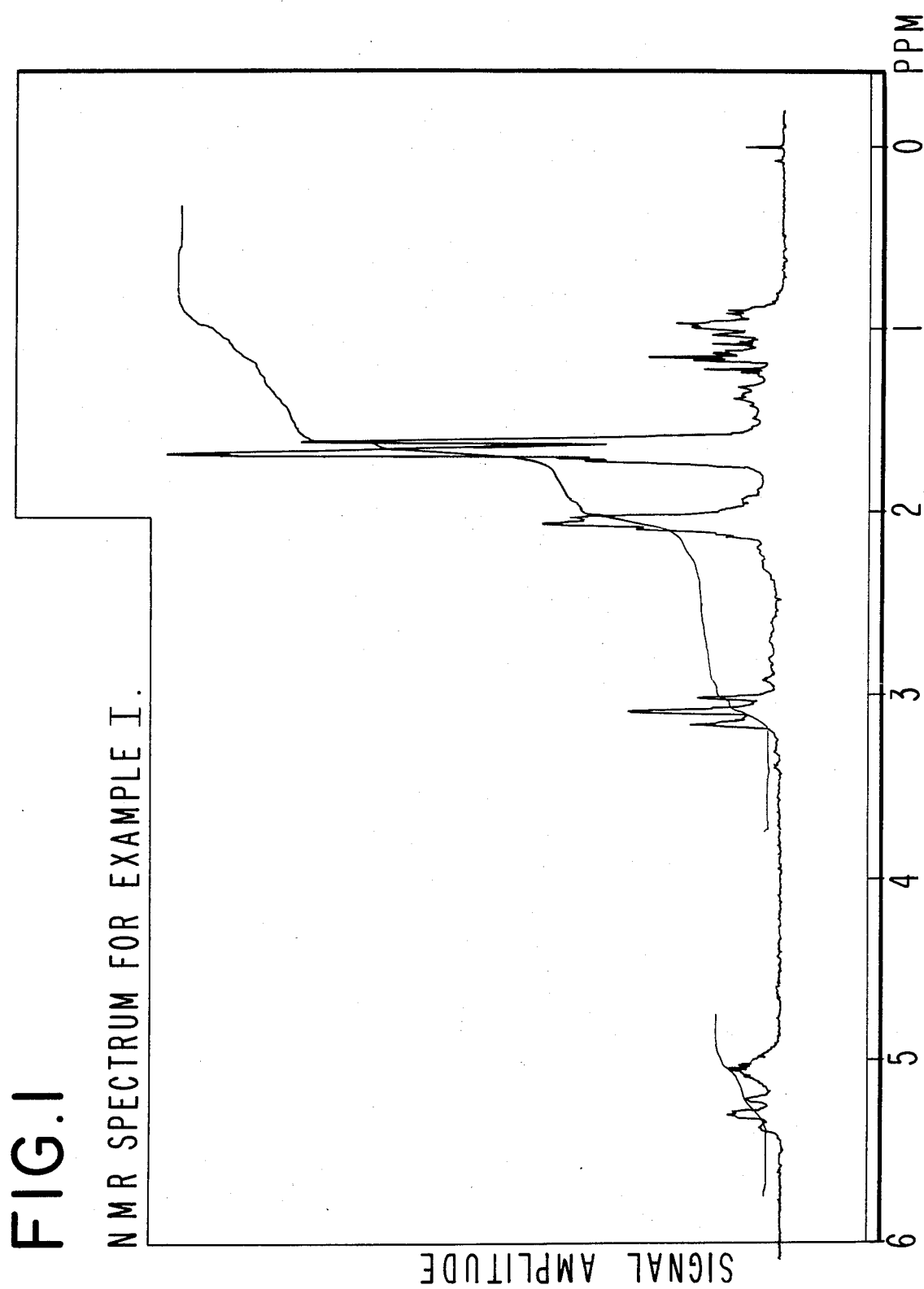
FIG. 1 is the NMR spectrum for thiogeranyl having the structure.

FIG. 1 is the NMR spectrum for the compound having the structure:

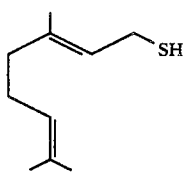

(Conditions: Field strength: 100 MHz; Solvent: CFCl₃).

EXAMPLE II

PREPARATION OF THIOGERANYL ISOVALERATE

Reaction

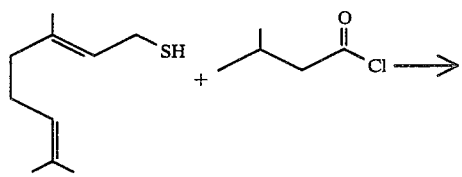

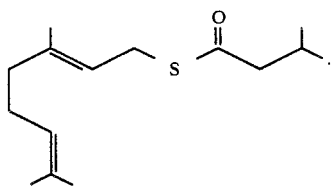

Into a 250 cc reaction flask equipped with stirrer, thermometer, reflux condenser and addition funnel is placed 100 ml methylene dichloride and 7.5 grams thiogeraniol. 5.0 Grams of triethylamine is then added to the reaction mass. Through the addition funnel 6.3 grams of isovaleryl chloride is added. With stirring, the reaction mass is heated to reflux and maintained at reflux for a period of 8 hours. At the end of the 8 hour period, the reaction mass is fractionally distilled yielding the compound having the structure:

This compound has a floral, grapefruit and roasted aroma and taste profile at 0.5 ppm causing it to be useful in grapefruit-flavored candy confections.

FIG. 2 is the GLC profile for the crude reaction product (Conditions: Carbowax column programmed at 100°–220° C. at 8° C. per minute).

FIG. 3 is the NMR spectrum for the compound having the structure:

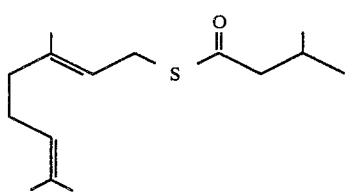

(Conditions: Field strength: 100 MHz; Solvent: CFCl₃).

EXAMPLE III

PREPARATION OF THIOGERANYL ESTER OF 2-METHYL-2-PENTENOIC ACID

Reaction

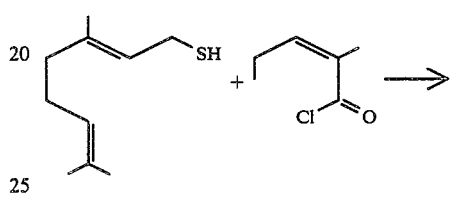

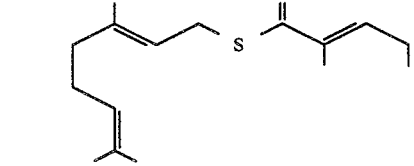

Into a 250 cc flask equipped with stirrer, thermometer, reflux condenser and heating mantle is placed 100 ml methylene chloride; 7.9 grams thiogeraniol and 5 grams of triethylamine. Through the addition funnel 6.6 grams of 2-methyl-2-pentenoyl chloride is added to the reaction mass over a period of one hour. The reaction mass, with stirring, is heated to reflux and maintained at reflux for a period of 8 hours. At the end of the 8 hour period, the reaction mass is cooled and fractionally distilled in a micro distillation apparatus yielding the following fractions:

| Fraction No | Vapor Temp. (°C.) | Liquid Temp. (°C.) | Vacuum mm/Hg. Pressure |
|---|---|---|---|
| 1 | 100 | 120 | 2 |
| 2 | 116 | 136 | 2 |
| 3 | 120 | 195 | 2 |

The resulting compound contained in essentially pure form in Fractions 2 and 3 has the structure:

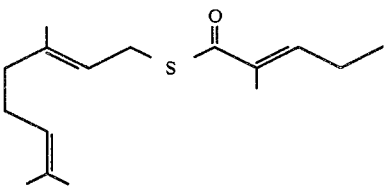

as confirmed by NMR, IR and mass spectral analyses. The resulting compound has a sulfury, fruity, oniony and floral aroma and taste profile at 1 ppm causing it to be useful in onion flavored foodstuffs, particularly epicurean onion soups.

FIG. 4 is the GLC profile for the crude reaction mass prior to distillation containing the compound having the structure:

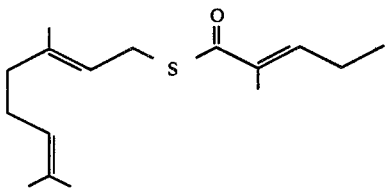

(Conditions: 8'×0.125" SE-30 column programmed at 100°-220° C. at 8° C. per minute).

FIG. 5 is the GLC profile for Fraction 2 of the foregoing distillation containing the compound having the structure:

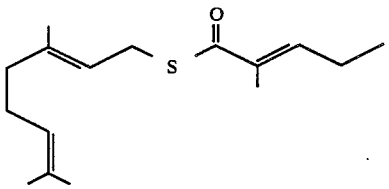

(Conditions: Carbowax column programmed at 220° C. isothermal).

FIG. 6 is the GLC profile of Fraction 3 of the foregoing distillation (Conditions: Carbowax column programmed at 220° C. isothermal).

FIG. 7 is the NMR spectrum for the compound having the structure:

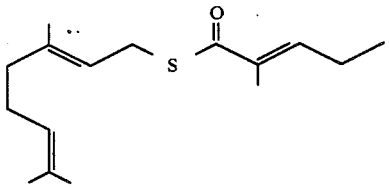

(Conditions: Field strength: 100 MHz; Solvent: CFCl$_3$).

EXAMPLE IV

PREPARATION OF THIOGERANYL ESTER OF ISOBUTYRIC ACID

Reaction

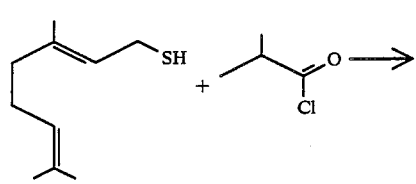

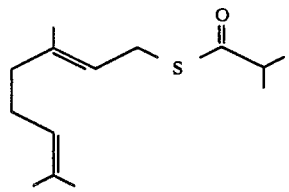

Into a 200 ml reaction flask equipped with heating mantle, addition funnel, magnetic stirrer, thermometer and reflux condenser are placed 7.5 grams thiogeraniol and 100 ml of methylene dichloride. The resulting mixture with stirring is admixed with 5 grams of triethylamine. Through the addition funnel over a period of 10 minutes, 5.3 grams of isobutyryl chloride is added to the reaction mass. The reaction mass with stirring is then heated to reflux and maintained at reflux for a period of 8 hours. At the end of the reflux period, the reaction mass is fractionally distilled yielding the compound having the structure:

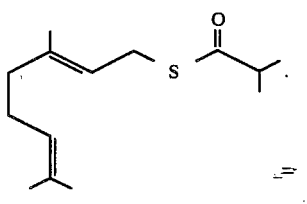

The compound having the structure:

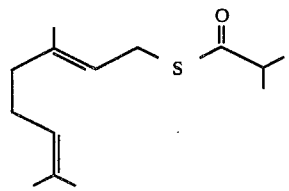

has a floral, carnation, guava and grapefruit aroma and taste profile at 1.0 ppm causing it to be useful in pineapple, grapefruit and guava flavored foodstuffs.

FIG. 8 is the GLC profile for the crude reaction product prior to distillation (Conditions: Carbowax column programmed at 100°-220° C. at 8° C. per minute).

FIG. 9 is the NMR spectrum for the compound having the structure:

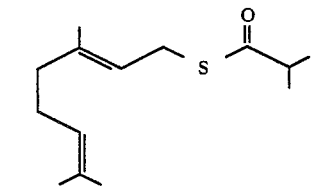

(Conditions: Field strength: 100 MHz; Solvent: CFCl$_3$).

EXAMPLE V

PREPARATION OF THIOGERANYL ESTER OF PROPIONIC ACID

REACTION

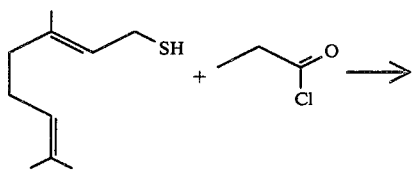

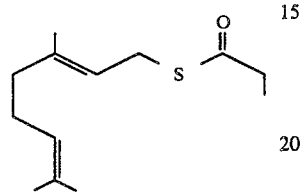

Into a 250 cc reaction flask equipped with stirrer, thermometer, reflux condenser, additional funnel and heating mantle is placed 100 ml methylene dichloride and 7.5 grams of thiogeraniol. 5 Grams of triethylamine is added to the reaction mass with stirring. With stirring through the addition funnel 5 grams of propionyl chloride is added to the reaction mass. The reaction mass is then heated to reflux and maintained at reflux for a period of 8 hours. At the end of the 8 hour period, the reaction product is fractionally distilled yielding the compound having the structure:

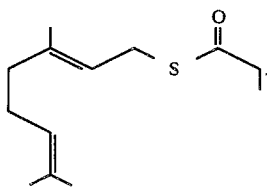

The compound having the structure:

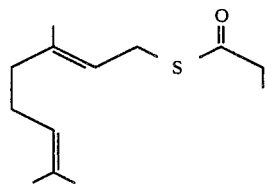

has a grapefruit and tomato aroma and taste profile at 0.5 ppm causing it to be useful in grapefruit, tomato and guava flavored foodstuffs.

FIG. 10 is the NMR spectrum for the compound having the structure:

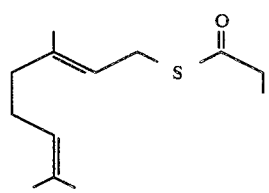

(Conditions: Field strength: 100 MHz; Solvent; CFCl₃).

EXAMPLE VI

PREPARATION OF THIOGERANYL ACETATE

Reaction

Into a 250 ml reaction flask equipped with stirrer, thermometer, reflux condenser, heating mantle and addition funnel is placed 100 ml methylene dichloride, 7.7 grams thiogeraniol and 5 grams triethylamine. With stirring, to the reaction mass over a period of 15 minutes is added 4 grams acetyl chloride. At the end of the addition of the acetyl chloride, the reaction mass is heated to reflux and refluxed for a period of 12 hours. At the end of the 12 hour period, the reaction mass is cooled and fractionally distilled yielding the compound having the structure:

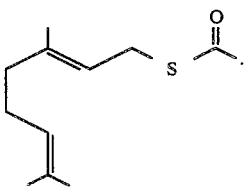

The compound having the structure:

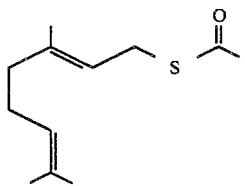

has an excellent floral, sulfury, galbanum, fruity and grapefruit aroma and taste profile at 0.1 ppm causing it to be useful in mint and grapefruit flavored foodstuffs.

FIG. 11 is the NMR spectrum for the compound having the structure:

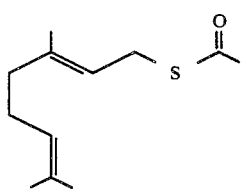

(Conditions: Field strength: 100 MHz; Solvent: CFCl₃).

EXAMPLE VII

FLORAL PERFUME COMPOSITION

The geranyl thio isobutyrate produced according to Example IV has an intense carnation and citrusy aroma profile. This material has great warmth and richness and blends well with many floral concepts. It is a rather unique floral note of great value to perfumery. It may be demonstrated by the following floral fragrance wherein the geranyl thio isobutyrate is used to the extent of 5% by weight.

The geranyl thio acetate produced according to Example VI has a floral galbanum and citrusy aroma with minty nuances. It is more floral and slightly less herbaceous than the isobutyrate. Formula "B", infra demonstrates the use of this material in a floral fragrance. The addition of 5% by weight of the geranyl thio acetate produced according to Example VI imparts intense floralcy and renders the fragrance more desirable as a perfume.

Both of these products perform well in fragrances and are judged to be very valuable fragrance materials:

| FLORAL FRAGRANCE | "A" | "B" |
|---|---|---|
| Citronellol | 12.3 | 12.3 |
| Geraniol | 2.5 | 2.5 |
| Amyl Cinnamic Aldehyde | 24.6 | 24.6 |
| Galaxolide ® 50 (Trademark Tricyclic Isochroman of International Flavors & Fragrances Inc.) | 9.8 | 9.8 |
| Vertenex High Cis (Cis-1-Butylcyclohexenyl Acetate Para Isomer) | 7.4 | 7.4 |
| Rose Oxide | 0.7 | 0.7 |
| Cinnamic Alcohol | 19.6 | 19.6 |
| Aldehyde C-11 (n-Undecylenic Aldehyde) | 0.5 | 0.5 |
| Aldehyde C-12 (n-Dodecyl Aldehyde in 10% solution in diethyl phthalate) | 0.5 | 0.5 |
| Citronellal (10% solution in diethyl phthalate) | 0.5 | 0.5 |
| Phenyl Ethyl Acetate | 2.5 | 2.5 |
| Ylang Oil | 1.2 | 1.2 |
| Indisan (Hydrogenated derivative of reaction product of Camphene and Resorcinol) | 3.7 | 3.7 |
| Musk Ketone | 5.0 | 5.0 |
| Oakmoss Resin | 0.5 | 0.5 |
| Liatrix Absolute (10% in diethyl phthalate) | 2.5 | 2.5 |
| Vetiver Acetate | 1.2 | 1.2 |
| Diethyl Phthalate | 5.0 | 5.0 |
| Geranyl thio isobutyrate produced according to Example IV | 5.0 | 0.0 |
| Geranyl thio acetate | 0.0 | 5.0 |

Thus, the fragrance containing the compound having the structure:

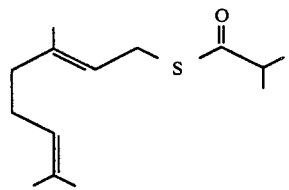

prepared according to Example IV can be described as "floral with a carnation undertone".

The fragrance containing the compound having the structure:

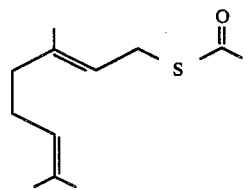

can be described as "floral with citrus and galbanum undertones and minty topnotes".

EXAMPLE VIII

PREPARATION OF COSMETIC POWDER

Cosmetic powder is prepared by mixing in a ball mill 100 grams of talcum powder with 0.25 grams of one of the products set forth in Table II, infra. The resulting materials have excellent perfume aromas as set forth in Table II, infra:

TABLE II

| Description of Composition | Fragrance Characteristics |
|---|---|
| Compound having the structure: 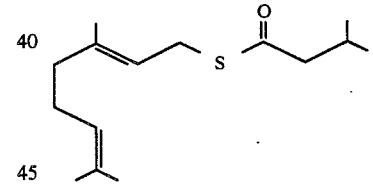 prepared according to Example II. | A citrusy and floral aroma profile. |
| Compound having the structure: 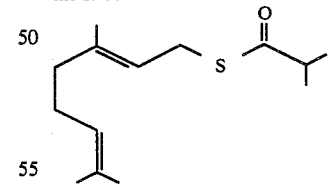 prepared according to Example IV. | A citrusy, floral aroma with carnation undertones. |
| Compound having the structure: 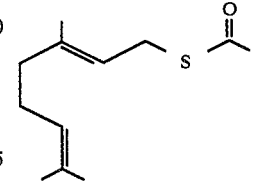 prepared according to Example VI. | A floral, citrusy and galbanum aroma profile with minty topnotes. |
| Perfume composition | A floral with a carnation |

TABLE II-continued

| Description of Composition | Fragrance Characteristics |
|---|---|
| of Example VII(A). | undertone. |
| Perfume composition of Example VII(B). | A floral with citrus and galbanum undertones and minty topnotes. |

EXAMPLE IX

CONCENTRATED LIQUID DETERGENTS

Concentrated liquid detergents with aromas as set forth in Table II of Example VIII, infra, (which detergents are produced from the Lysine salt of n-dodecyl benzene sulfonic acid, as more specifically described in U.S. Pat. No. 3,948,818 issued on Apr. 6, 1976 the specification for which is incorporated by reference herein) are prepared containing one of the substances set forth in Table II of Example VIII, supra. They are prepared by adding and homogeneously mixing the appropriate quantity of substance set forth in Table II of Example VIII, supra in the liquid detergent. The detergents all possess excellent aromas as set forth in Table II of Example VIII, supra.

EXAMPLE X

PREPARATION OF COLOGNES AND HANDKERCHIEF PERFUMES

Perfume compositions containing one of the substances set forth in Table II of Example VIII having aromas as set forth in Table II of Example VIII are incorporated into colognes at concentrations of 1.5%, 2.0%, 2.5%, 3.0%, 3.5%, 4.0% and 5.0% in 80%, 85%, 90% and 95% aqueous food grade ethanol; and into handkerchief perfumes at concentrations of 10%, 15%, 20%, 30%, 40% and 50% (in 90% and 95% aqueous food grade ethanol). Distinct and definitive fragrance aromas as set forth in Table II of Example VIII, supra are imparted to the colognes and to the handkerchief perfumes.

EXAMPLE XI

PREPARATION OF SOAP COMPOSITIONS

One hundred grams of soap chips (obtained from IVORY ® Soap) (a Trademark of the Procter & Gamble Company of Cincinnati, Ohio) are mixed with 2 grams of each of the materials set forth in Table II of Example VIII, supra until substantially homogeneous compositions are obtained. The resulting compositions are melted at a 180° C. for a period of 4 hours under 8 atmospheres nitrogen pressure. The resulting melts are cooled and formed into soap bars. Each of the soap bars have aromas as set forth in Table II of Example VIII, supra.

EXAMPLE XII

PREPARATION OF LIQUID DETERGENTS

Concentrated liquid detergents with aromas as set forth in Table II of Example VIII, supra containing 0.2%, 0.5% and 1.2% of the compositions as set forth in Table II of Example VIII, supra are prepared by adding the appropriate quantity of the compositions as set forth in Table II of Example VIII, supra to a liquid detergent known as P-87. The aromas of the liquid detergent increase with increasing concentrations of the composition set forth in Table II of Example VIII, supra.

EXAMPLE XIII

Utilizing the procedure of Example I at Column 15 of U.S. Pat. No. 3,632,396 the specification for which is incorporated by reference herein, a non-woven cloth substrate useful as a dryer-added fabric softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of one of the perfumants set forth in Table II of Example VIII, supra having the properties set forth in Table II of Example VIII, supra.

Fabric-softening compositions prepared as set forth above having the aroma characteristics set forth in Table II of Example VIII, supra essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II of Example VIII, supra are imparted in a pleasant manner to the head space in the dryer on operation thereof using the said dryer added fabric softening non-woven fabric.

EXAMPLE XIV

PERFUMED LIQUID DETERGENTS

Concentrated liquid detergents having aromas as set forth in the Table II of Example VIII, supra are prepared containing 0.10%, 0.15%, 0.20%, 0.40% and 0.80% of one of the materials as set forth in Table II of Example VIII, supra. They are prepared by adding and homogeneously mixing the appropriate quantities of perfume substance (as set forth in Table II of Example VIII, supra) in the liquid detergents. The liquid detergent is a builder-free liquid detergent consisting of (a) 50% of a non-ionic surfactant having an HLB of 8.0 and a critical micelle concentration of 0.007 weight percent at 25° C.; (b) an ionic surfactant which is triethanolamine citrate; and (c) one weight percent of diethanolamine prepared according to United Kingdom Patent Specification No. 1,491,603 the specification for which is incorporated by reference herein.

The detergents all posses fragrances as set forth in Table II of Example VIII, supra, intensity increasing with greater concentrations of fragrance material.

EXAMPLE XV

GRAPEFRUIT FLAVOR FORMULATION

The following mixture is prepared:

| Ingredients | Parts by Weight |
|---|---|
| Nootkatone | 4.0 |
| Grapefruit oil | 1.5 |
| Para-menthane thiol | 0.2 |
| One of the thiogeranyl esters set forth below: | 4.2 |

| Ingredients | Parts by Weight |
|---|---|
| Example XV(A): The compound having the structure: 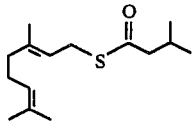 prepared according to Example II. | |
| Example XV(B): The compound having the structure: 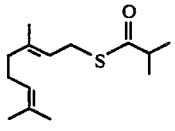 prepared according to Example IV. | |
| Example XV(C): The compound having the structure: 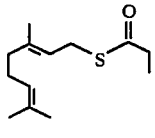 prepared according to Example V. | |
| Example XV(D): The compound having the structure: 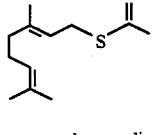 prepared according to Example VI. | |

Each of Examples XV(A), XV(B), XV(C) and XV(D) contains one of the thiogeranyl esters of our invention. Each of the thiogeranyl esters of our invention imparts a natural-like, "tropical fruit" nuance to the grapefruit flavor.

When each of the grapefruit flavors of Examples XV(A), XV(B), XV(C) and XV(D) are separately added to a grapefruit marmalade, the resulting grapefruit marmalade has a more natural-like, pleasant tasting, tropical fruit nuance than without the thiogeranyl esters of our invention. A blind bench panel of five members not associated with the instant invention unanimously prefers the grapefruit marmalades containing the thiogeranyl esters of Examples XV(A), XV(B), XV(C) and XV(D) to the grapefruit marmalade not containing said thiogeranyl esters.

EXAMPLE XVI

A. POWDER FLAVOR COMPOSITION

20 Grams of the flavor composition of Example XV is emulsified in a solution containing 300 grams gum acacia and 70 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. SUSTAINED RELEASE FLAVOR

The following mixture is prepared:

| Ingredients | Parts by Weight |
|---|---|
| Liquid grapefruit flavor composition of Example XV | 20.0 |
| Propylene glycol | 9.0 |
| Cab-O-Sil ® M-5 (Brand of Silica produced by the Cabot Corporation of 125 High Street, Boston, Mass. 02110; Physical Properties: Surface area: 200 m²/gm Nominal particle size: 0.012 microns Density: 2.3 lbs./cu. ft.) | 5.00 |

The Cab-O-Sil is dispersed in the grapefruit flavor composition of Example XV with vigorous stirring, thereby resulting in a viscous liquid. 71 Parts by weight of the powder flavor composition of Part "A", supra, is then blended into the said viscous liquid, with stirring, at 25° C. for a period of 30 minutes resulting in a dry, free flowing sustained release flavor powder.

EXAMPLE XVII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XV is added to the solution which is then homogenized to form an emulsion having particle size typically in the range of 5–40 microns. This material is kept at 120° F. under which conditions the gelatin will not jell.

Coacervation is induced by adding, slowly and uniformly 40 parts by weight of 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XVIII

CHEWING GUM

100 Parts by weight of chicle are mixed with 4 parts by weight of the flavor prepared in accordance with Example XVI(B). 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting grapefruit flavor.

EXAMPLE XIX

CHEWING GUM

100 Parts by weight of chicle are mixed with 18 parts by weight of the flavor prepared in accordance with Example XVII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting grapefruit flavor.

EXAMPLE XX

TOOTHPASTE FORMULATION

The following separate groups of ingredients are prepared:

| Parts by Weight | Ingredient |
| --- | --- |
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (Dihydrate) |
| Group "C" | |
| 2.000 | Sodium N—Lauroyl Sarcosinate (foaming agent) |
| Group "D" | |
| 1.200 | Flavor Material of Example XVII |
| 100.000 | (TOTAL) |

1. The ingredients in Group "A" are stirred and heated in a steam jacketed kettle to 160° F.
2. Stirring is continued for an additional 3 to 5 minutes to form a homogeneous gel.
3. The powders of Group "B" are added to the gel while mixing, until a homogeneous paste is formed.
4. With stirring, the flavor of "D" is added and lastly the sodium-n-lauroyl sarcosinate.
5. The resultant slurry is then blended for one hour. The completed paste is then transferred to a 3-roller mill and the homogenized and finally tubed.

The resulting toothpaste when used in a normal toothbrushing procedure yields a pleasant grapefruit flavor, of constant strong intensity throughout said procedure (1–1.5 minutes).

EXAMPLE XXI

CHEWABLE VITAMIN TABLETS

The flavor material produced according to the process of Example XVII is added to a Chewable Vitamin Tablet Formulation at a rate of 10 gm/Kg which chewable vitamin tablet formulation is prepared as follows:

In a Hobart Mixer, the following materials are blended to homogeneity:

| Ingredients | Gms/100 Tablets |
| --- | --- |
| Vitamin C (ascorbic acid) as ascorbic acid-sodium mixture 1:1 | 70.00 |
| Vitamin B$_1$ (thiamine mononitrate) as Rocoat ® thiamine mononitrate 33⅓% (Hoffman La Roche) | 4.00 |
| Vitamin B$_2$ (riboflavin) as Rocoat ® riboflavin 33⅓% | 5.00 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XVII | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant long-lasting, consistently strong grapefruit flavor for a period of 12 minutes.

What is claimed is:

1. The thiogeranyl ester having the structure:

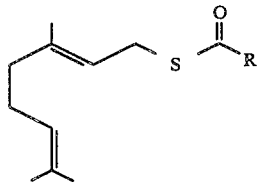

wherein R represents C$_1$–C$_4$ alkyl or 2-(2-pentenyl).

2. The thiogeranyl ester of claim 1 having the structure:

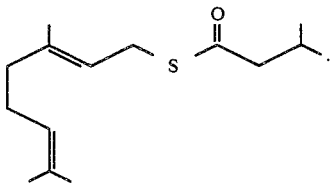

3. The thiogeranyl ester of claim 1 having the structure:

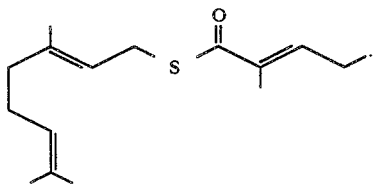

4. The thiogeranyl ester of claim 1 having the structure:

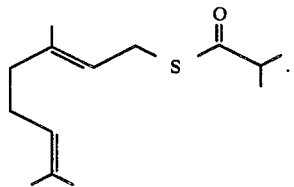

5. The thiogeranyl ester of claim 1 having the structure:

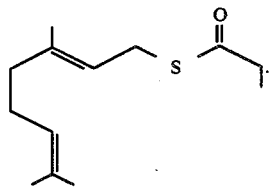

6. The thiogeranyl ester of claim 1 having the structure:

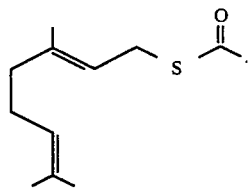

7. A process for augmenting or enhancing the aroma or taste of a consumable material selected from the group consisting of perfume compositions, colognes, perfumed articles, foodstuffs, chewing gums, toothpastes and medicinal products comprising the step of intimately admixing with said consumable material, an aroma or taste augmenting or enhancing quantity of the thiogeranyl ester of claim 1.

8. The process of claim 7 wherein the consumable material is a perfume composition, cologne or perfumed article.

9. The process of claim 7 wherein the consumable material is a foodstuff, chewing gum, toothpaste or medicinal product.

* * * * *